United States Patent
Nuhu et al.

(10) Patent No.: US 9,316,629 B2
(45) Date of Patent: Apr. 19, 2016

(54) METHOD OF DETERMINING PHENOXY HERBICIDES IN WATER SAMPLES BY PHASE TRANSFER MICROEXTRACTION WITH SIMULTANEOUS DERIVATIZATION AND GAS-CHROMATOGRAPHY MASS-SPECTROMETRY ANALYSIS

(71) Applicant: KING FAHD UNIVERSITY OF PETROLEUM AND MINERALS, Dhahran (SA)

(72) Inventors: Abdulmumin A. Nuhu, Dhahran (SA); Chanbasha Basheer, Dhahran (SA); Khalid Alhooshani, Dhahran (SA); Abdul Rahman Al-Arfaj, Dhahran (SA)

(73) Assignee: King Fahd University of Petroleum and Minerals, Dhahran (SA)

(*) Notice: Subject to any disclaimer, the term of this patent is extended or adjusted under 35 U.S.C. 154(b) by 202 days.

(21) Appl. No.: 14/031,658

(22) Filed: Sep. 19, 2013

(65) Prior Publication Data

US 2015/0079692 A1 Mar. 19, 2015

(51) Int. Cl.
*G01N 30/02* (2006.01)
*G01N 33/18* (2006.01)
*G01N 30/72* (2006.01)
*G01N 30/06* (2006.01)

(52) U.S. Cl.
CPC ........ *G01N 33/1826* (2013.01); *G01N 30/7206* (2013.01); *G01N 2030/067* (2013.01)

(58) Field of Classification Search
None
See application file for complete search history.

(56) References Cited

U.S. PATENT DOCUMENTS

| 6,780,314 B2 | 8/2004 | Jinno et al. |
| 2010/0155304 A1 | 6/2010 | Ding et al. |
| 2011/0309001 A1* | 12/2011 | Soane et al. ......... 208/390 |

FOREIGN PATENT DOCUMENTS

| CN | 101776657 A | 7/2010 |
| EP | 1 010 974 A1 | 6/2000 |
| JP | 63-48269 | 2/1988 |

OTHER PUBLICATIONS

Catalina, M.I., et al. Determination of chlorophenoxy acid herbicides in water by in situ esterification followed by in-vial liquid—liquid extraction combined with large-volume on-column injection and gas chromatography—mass spectrometry, 2000, Journal of Chromatography A, vol. 877, pp. 153-166.*

Miki, A. et al., GC and GC-MS Determination of Fluoroacetic Acid and Phenoxy Acid Herbicides via Triphasal Extractive Pentafluorobenzylation Using a Polymer-Bound Phase-Transfer Catalyst, 1998, JOurnal of Analytical Toxicology, vol. 22, pp. 237-245.*

* cited by examiner

*Primary Examiner* — Robert Xu
(74) *Attorney, Agent, or Firm* — Oblon, McClelland, Maier & Neustadt, L.L.P

(57) ABSTRACT

A method for determining the concentration of a phenoxy herbicide in an aqueous sample, by simultaneously phase-transfer catalyst extracting and alkylating an aqueous sample comprising a phenoxy herbicide to form a sample composition, and measuring an amount of the alkylated phenoxy herbicide in the sample composition. The method includes controlling factors such as pH of the aqueous matrix, temperature, extraction duration, type and amount of derivation reagents, and type and amount of phase transfer catalyst.

15 Claims, 4 Drawing Sheets

METHOD OF DETERMINING PHENOXY HERBICIDES IN WATER SAMPLES BY PHASE TRANSFER MICROEXTRACTION WITH SIMULTANEOUS DERIVATIZATION AND GAS-CHROMATOGRAPHY MASS-SPECTROMETRY ANALYSIS

BACKGROUND OF THE INVENTION

1. Field of the Disclosure

The present invention relates to method for the determination of phenoxy herbicides, e.g., 4-chloro-2-methylphenoxy acetic acid and 4-chloro-2-methylphenoxy propionic acid, in water. The method utilizes a phase transfer catalyst-assisted micro extraction with simultaneous derivatization.

2. Description of Related Art

Following the first reported synthesis of phenoxyherbicides (PHs) in the 1940s, many different types of PHs can now be found. For example, 2,4-dichlorophenoxyacetic (2,4-D), one of the most studied of the PHs, falls within the sub-type, phenoxyacetic acids (Tuxen, N., Reitzel, L. A., Albrechtsen, H.-J., Bjerg, P. L., Ground Water, 2006, 44 256-265-incorporated by reference in its entirety). Other sub-types include phenoxybutyric acids and phenoxypropionic acids. Recently, the syntheses of two new acetate types, 2-chlorophenoxyacetate (2CPA) and 2,4,5-trichlorophenoxyacetate (TCPA), were accomplished (Sarijo, S. H., Bin Hussein, M Z., Yahaya, A. H. J., Zainal, Z., Yarmo, M. A, Current Nanoscience, 2010, 6, 199-205—incorporated by reference in its entirety). Due to the widespread use of PHs, traces of the compounds can now be found in various environmental matrices, such as rivers and drinking water, municipal landfills, in coral Galaxeafascicularis, and in the atmosphere (Marchese, S., Perret, D., Gentili, A., D'Ascenzo, G., Faberi, A., Rapid Commun. Mass Spectrom, 2002, 16, 134-141; Gintautas, P. A., Daniel, S. R., Macalady, D. L., Environ. Sci. Technol, 1992, 26, 517-521; Sabdono, A., Radjasa, O. K., Kang, S., Hur, H.-G., Grossart, H.-P., Simon, M., Zocchi, E., Risk, M. J., Res. J. Env. Toxicol, 2007, 1, 71-77; Waite, D. T., Bailey, P., Sproull, J. F., Quiring, D. V., Chau, D. F., Bailey, J., Cessna, A. J., Chemosphere, 2005, 58, 693-703—incorporated by reference in its entirety).

Following this concern, toxicity studies carried out on different types of PHs indicate a non-specific mode of action through the sub-mitochondrial particle assay with EC50 values ranging between 21 µM and 110 µM (Argese, E., Bettiol, C., Marchetto, D., De Vettori, S., Zambon, A., Miana, P., Ghetti, P. F., Toxicol. in Vitro, 2005, 19, 1035-1043—incorporated by reference in its entirety). The LD50 for male rats is 370 mg kg-1 body weight for 2,4-dichlorophenoxyacetic acid and 700 mg kg-1 body weight for 4-chloro-2-methyl phenoxyacetic acid (CMPA), indicating a slight toxicity (Grabinska-Sota, E., Wisniowska, E., Kalka, J., Crop Protection, 2003, 22, 355-360—incorporated by reference in its entirety). Data on the carcinogenicity, genotoxicity, and mutagenicity of PHs are inconsistent. However, long-term exposure of PHs indicate a strong association of cancer exposure. This toxicity may be explained by free radical formation in humans (Bukowska, B., Rychlik, B., Krokosz, A., Michalowicz, J., Food Chem. Toxicol, 2008, 46, 359-367—incorporated by reference in its entirety). Trace level of PHs detected in the water supplies may represent a potential danger to the living organisms such as plants, animals and possibly humans (Michalowicz, J., Polish J. Environ. Studies, 2005, 14, 327-333; Sterling, T. D., Arundel, A. V., Scand. J. Work Environ. Health, 1986, 12, 161-173—incorporated by reference in its entirety). Thus, it has become especially important to evaluate PHs-contaminated water at trace level.

For quantitative determination of PHs, different extraction and preconcentration methods have been applied for various matrices. Three dimensional liquid microextraction, liquid-liquid-liquid microextraction, was used for bovine milk samples (Zhu, L., Ee, K. H., Zhao, L., Lee, H. K., J. Chromatogr. A, 2002, 963, 335-343—incorporated by reference in its entirety). For the extraction and preconcentration of 2,4-dichlorophenoxyacetic acid, two types of extraction solvents, methanol/acetic acid (99:1) and propanone/water/acetic acid (80:19:1) were used for high humic matter soils that were agitated overnight (Merini, L. J., Cuadrado, V., Giulietti, A. M., Chemosphere, 2008, 71, 2168-2172—incorporated by reference in its entirety). As an example of good PHs recoveries with minimal retention on the sorbent, the use of a dynamic ion-exchange solid-phase extraction (DIE-SPE) was employed (Li N., Lee H. K., Anal. Chem., 2000, 72, 3077-3084—incorporated by reference in its entirety). Furthermore, the efficiency of (DIE-SPE) was highly dependent upon using the correct sorbent. Activated carbon prepared from coals and coconut shells have recently shown great potentials as sorbents for the extraction of PHs from aqueous solutions (Ignatowicz, K., J. Hazard. Mater, 2009, 169, 953-957—incorporated by reference in its entirety). On the other hand, 2,4-dichlorophenoxyacetic acid was more amenable for sorption than other compounds tested because of its limited solubility. As an alternative to using liquid extraction and as an effort to minimize the solvent volume consumed, solid phase microextraction (SPME) could be performed; however, an automated on-line in-tube SPME was performed, and yet, only a dismal extraction recovery (23.9-30.0%) resulted (Takino, M., Daishima, S., Nakahara, T., Analyst, 2001, 126, 602-608—incorporated by reference in its entirety). The recovery via SPME was determined by electrospray ionization mass-spectrometry (ESI-MS) following separation of the analytes through a liquid chromatography column.

Other means of quantitative determination of these compounds include HPLC/diode array detector (DAD), GC-MS, and capillary electrophoresis with ultraviolet detection (CE-UV) (Crespin, M. A., Gallego, M., Valcarcel, M., Gonzalez, J. S., Environ. Sci. Technol, 2001, 35, 4265-4270; Kumar, A., Malik, A. K., Pico, Y., Electrophoresis, 2010, 31, 2115-2125—incorporated by reference in its entirety). The determination of polar and ionizable analytes using GC-MS is problematic due to the difficulty in extracting these types of analytes into organic solvents but also as a result of the poor thermal characteristics of polar analytes typically associated with GC. Chemical derivatization is, therefore, better suited to assist in such determinations of PHs. Using two derivatization reagents, pentylfluorobenzyl bromide and benzyl bromide, low-yield aqueous-phase derivatization was obtained in the SPME-GC-MS method, resulting in a higher detection limit (LOD) (1 µg l$^{-1}$) (Nilsson, T., Baglio, D., Galdo-Migueza, I., Madsen, J. O., Facchetti, S., J. Chromatogr. A, 1998, 826, 211-216—incorporated by reference in its entirety). In contrast, a different SPME-GC-MS method was reported for phenoxy acid derivatives of butyl chloroformate, but it was also met with a high standard deviation of 20-50% (Henriksen, T., Svensmark, B., Lindhardt, B., Juhler, R. K., Chemosphere, 2001, 44, 1531-1539—incorporated by reference in its entirety).

BRIEF SUMMARY

An objective of the invention is a single step method that can overcome the problems associated with quantitation of PHs at trace levels. The present invention is to provide a method for the determination of phenoxy herbicides, such as 4-chloro-2-methylphenoxy acetic acid (MCPA) and 4-chloro-2-methylphenoxy propionic acid (MCPP), in water.

In another embodiment the method utilizes a phase transfer catalyst-assisted micro extraction with simultaneous derivatization.

In another embodiment of the invention the method combines simultaneous cloud-point extraction and alkylation of a phenoxy herbicide, with phase transfer catalysis using a quaternary ammonium compound which forms neutral ion-paired analytes in the extraction solvent.

In one aspect of the invention phase transfer catalysis is performed in order to facilitate the enrichment of GC-suitable organic solvents with polar analytes.

In another aspect of the invention when surfactants are employed, extraction and phase separation can be achieved by heating the surfactant above its cloud point temperature.

DETAILED DESCRIPTION

Figure 1:
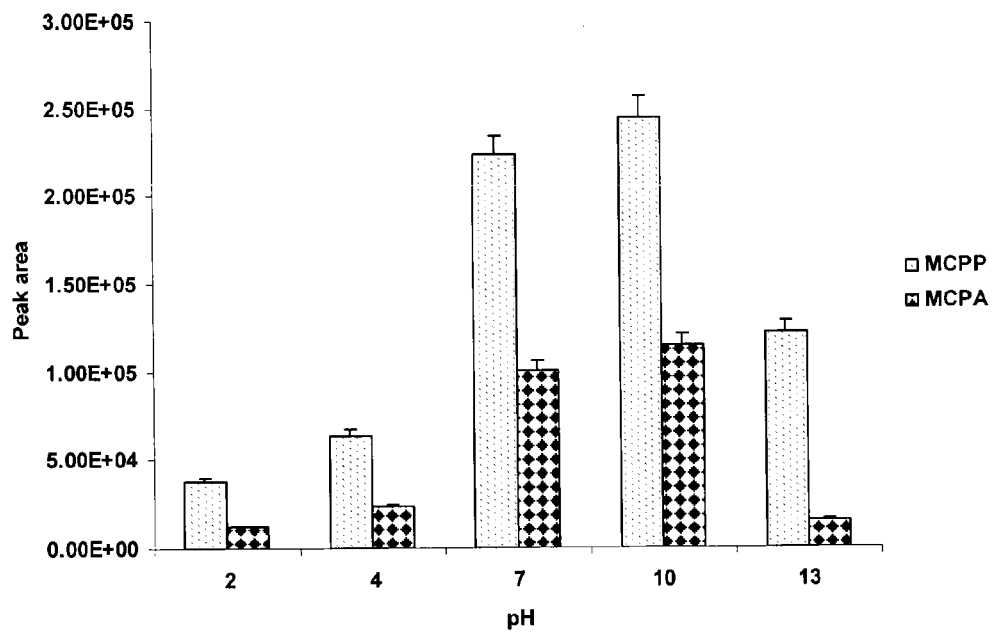
FIG. 1 is a graph of peak area versus pH for CPE procedure on MCPP and MCPA.

The term single step method as used herein refers to phase-transfer catalyst extracting and alkylating at the same time. The term single step method does not exclude preparing, mixing, and heating an aqueous sample prior to the phase-transfer catalyst extracting and alkylating, or measuring the amount of alkylated phenoxy herbicide after the phase-transfer catalyst extracting and alkylating. The single step method is able to determine the concentration of phenoxy herbicides at trace levels, e.g., ranging from 0.1 to 80 $\mu gl^{-1}$.

A phenoxy herbicide is any member of a family of chemicals related to the growth hormone indoleacetic acid. Phenoxy herbicides are further grouped into phenoxyacetic, phenoxybutyric and phenoxypropionic subtypes. Chemically phenoxy herbicides are acids, and are typically applied in an ester or salt form. Examples of phenoxy herbicides include 4-chloro-2-methylphenoxy acetic acid (MCPA), 4-chloro-2-methylphenoxy propionic acid (MCPP), 2-chlorophenoxyacetic acid (2CPA), and 2,4,5-trichlorophenoxyacetic acid (TCPA).

Phase transfer catalyst-assisted micro extraction is a process of extracting with a phase transfer catalyst which facilitates the migration of an analyte from one phase into another phase where reaction occurs. Ionic reactants are often soluble in an aqueous phase but insoluble in an organic phase in the absence of the phase transfer catalyst. The catalyst helps solubilize the salts into the organic phase. Examples of suitable phase transfer catalysts include tetramethyl ammonium hydroxide and tetrabutyl ammonium hydroxide, preferably tetrabutyl ammonium hydroxide.

Phase transfer catalysis refers to the acceleration of the reaction upon the addition of the phase transfer catalyst. Phase transfer catalysis is performed in order to facilitate the enrichment of GC-suitable organic solvents with polar analytes.

When surfactants are employed for this purpose, extraction and phase separation can be achieved by heating the surfactants above its cloud point temperature. This is called cloud-point extraction (CPE). Cloud point temperature is the temperature at which dissolved solids are no longer completely soluble, precipitating as a second phase giving the fluid a cloudy appearance. The cloud point of a nonionic surfactant is the temperature where the mixture starts to phase separate and two phases appear.

The addition of surfactants is optional. Phase transfer catalysis can also be performed without surfactants.

Phase transfer catalysis may be performed using a quaternary ammonium compound which forms neutral ion-paired analytes in the extraction solvent. Examples of the quaternary ammonium compound include tetramethyl ammonium hydroxide and tetrabutyl ammonium hydroxide.

The selection of extraction solvent is very important to the distribution of analytes between the aqueous and organic phases during phase transfer catalysis (Wu, J., Lee, H. K., Anal Chem, 2006, 78, 7292-7301—incorporated by reference in its entirety). To make it easier for the analyte-rich organic phase to be obtained after the phase transfer, a solvent with a density less than that of the aqueous phase is desirable. The extraction solvent may be selected from the group consisting of 1-octanol, ethyl acetate, n-hexane and toluene. The extraction solvent is preferably toluene.

Derivatization is a technique which transforms a chemical compound into a derivative. Generally, a specific functional group of the compound participates in the derivatization reaction and transforms a substance extracted from a mixture to a derivate of different reactivity, solubility, boiling point, melting point, aggregate state, or chemical composition. The resulting new chemical properties can be used for quantification or separation of the extracted substance, making it useful for chemical analysis of mixtures.

In the present invention, in order to carry out derivatization, an extracted aqueous composition comprising a phenoxy herbicide is alkylated. Alkylation is the transfer of an alkyl group from one molecule to another. The alkyl group may be transferred as an alkyl carbocation, a free radical, a carbanion, a carbene, or an equivalent thereof. The alkylation includes methylation or ethylation, preferably methylation. Examples of alkylating agents include alkyl halides and alcohols, preferably an alkyl halides. The halide is preferably bromide, chloride, or iodide. The alkyl halide is more preferably methyl iodide or ethyl bromide, especially preferably methyl iodide.

The pH of the aqueous phase may be a controlling factor in phase transfer catalysis and hence its influence on the microextraction process. Thus, the analytes need to be ionized in order to form ion-pairs with PTC which will then facilitate their partitioning into the organic phase. With MCPA and MCPP having pKa values around 3.22 and 3.38 respectively, the pH of the analyte solution must be greater than 5 to effect sufficient ionization of the analytes (Behrens, R., Morton, H. L., Plant Physiol, 1963, 38, 165-170—incorporated by reference in its entirety). Therefore, the pH is preferably from 7 to 13, and especially preferably about 10.

Acidic buffer solutions may be used to control the pH of the aqueous phase. The acidic buffer solution may be citric acid/ hydrochloric acid/sodium chloride or a solution prepared from anhydrous sodium acetate and glacial acetic acid.

Temperature may also play a very important role in phase transfer catalyst-assisted microextraction (PME) procedure by enhancing phase transfer and preconcentration factors of analytes (Chen, J., Chen, H., Jin, X., Chen, H., Talanta, 2009, 77, 1381-1387-incorporated by reference in its entirety). The preferred temperature is about 70° C.

The present method may also be carried out with an internal standard.

EXAMPLES

Reagents and Chemicals

Spectrometric grade reagents were used throughout the various experiments. Certified alkaline and neutral buffer solutions were supplied by Fischer Chemical Ltd (St. Louis, Mo.). Acidic buffer solution of pH 2 (citric acid/hydrochloric acid/sodium chloride) was supplied by Sigma-Aldrich and pH 4 solution was prepared from anhydrous sodium acetate (BDH Chemicals Ltd, VWR, USA) and glacial acetic acid (Win lab Ltd, Leicestershire, UK). Ethyl bromide and methyl iodide were supplied by Fluka, AG. Phase transfer catalysts (PTC), tetramethyl ammonium hydroxide (TMA-OH) and tetrabutyl ammonium hydroxide (TBA-OH), were purchased from BDH Chemicals Ltd (Poole, England). MCPA and MCPP were obtained from Supeico (Bellefonte, Pa.). 1 µg ml$^{-1}$ stock standard solutions were prepared in acetone from which dilutions were made as required. Ultra pure water was prepared in the laboratory using Nanopure water purification (Barnstead, Dubuque, Iowa, USA) system. All standards used were of 97% purity or better.

Instrumentation

MCPP and MCPA were resolved on an Agilent GC-MS 6890N system equipped with autosampler 7683B series and a 6890B injector. An Agilent 19091Z-213 column of 30 m×320 µm dimensions, having an HP-1 methyl siloxane stationary phase and film thickness of 1 µm was used. High purity helium flowing at a rate of 1.5 ml min$^{-1}$ was employed as the carrier gas. The column temperature program was initially set at 50° C. held for 5 min, and then ramped to 150° C. at a rate of 5° C. min$^{-1}$. This was followed immediately by another ramping to 210° C. at 10° C. min$^{-1}$ and held at this temperature for 4 min to achieve the total run time of 35 min. Auxiliary and ion source temperatures were both set at 280° C. and 230° C. respectively. The injector was set in the splitless mode with injection volume of 1 µl. Total ion current in SCAN mode for ions of masses between 50 and 550 was used for peak identification. Selective ion monitoring (SIM) mode was used for quantification of analytes. The m/z of 214 and 228 was used for methylated MCPA and MCPP, respectively; m/z of 228 and 242 was used for ethylated MCPA and MCPP, respectively.

Water Sample Collection

Seawater samples were collected from a total of four stations in an eastern province of Saudi Arabia. Two of the stations, DS-1 and DS-2, are situated around Dammam Corniche, an area considered to be highly polluted with inputs from sewage disposal points and agricultural run-off water. The two other collection sites, JS-3 and JS-4, are locations within Jubail Port. There are oil filling terminals and industrial cooling water discharge points in the JS-3 and JS-4 locations.

At the time of collection, the seawater samples were collected in plastic bottles, in order to minimize adsorption of the polar analytes, and then chilled in ice. The salt content of these samples was between 38.35 and 41.45 parts per thousand. The samples were extracted without additional sample pre-treatment.

Phase Transfer Microextraction and Derivatization Procedure

A mixture of the analytes (spiked at 20 µg l$^{-1}$), derivatization reagent (228 mg of CH$_3$I), and PTC (1.6 ml of TBA-OH) was added to 10 ml of ultrapure water (pH adjusted 10) in a 20 ml glass vial and vortexed for 30 sec. 500 µl of toluene was added to the sample solution and heated to 70° C. for 60 min. The phase transfer microextraction and simultaneous derivatization were performed with magnetic agitation at 1250 rpm. Then the cloudy suspension was obtained, which separated into two distinct phases after centrifuging at 4000 rpm for 5 min. The derivatized extract was injected into the GC-MS for analysis. Choice of solvent, extraction time, type and amount of derivatization reagent, type and amount of PTC, pH, and temperature were fine-tuned to optimize the efficiency of the extraction and derivatization procedures.

Five pH values that included acidic, basic, and neutral points, were tested. The comparative results obtained for pH values 2, 4, 7, 10, and 13 are presented in FIG. 1.

FIG. 1 shows an effect of pH on CPE procedure at experimental conditions of 20 µg l$^{-1}$ analyte concentration, 3.2 ml TBA-OH (0.5 moll$^{-1}$), 60 min extraction time, 228 mg MeI and 500 µl of toluene as extractant solvent at 70° C. From the results obtained, the largest enrichment factors (Us) were recorded for both analytes at pH 10. Therefore, this pH is preferred and most favorable to the ionization of the analytes under the experimental conditions.

As extraction solvents, 1-octanol, ethyl acetate, n-hexane and toluene with respective densities (g cm$^{-3}$) of 0.824, 0.897, 0.655 and 0.867 were tested.

Figure 2:
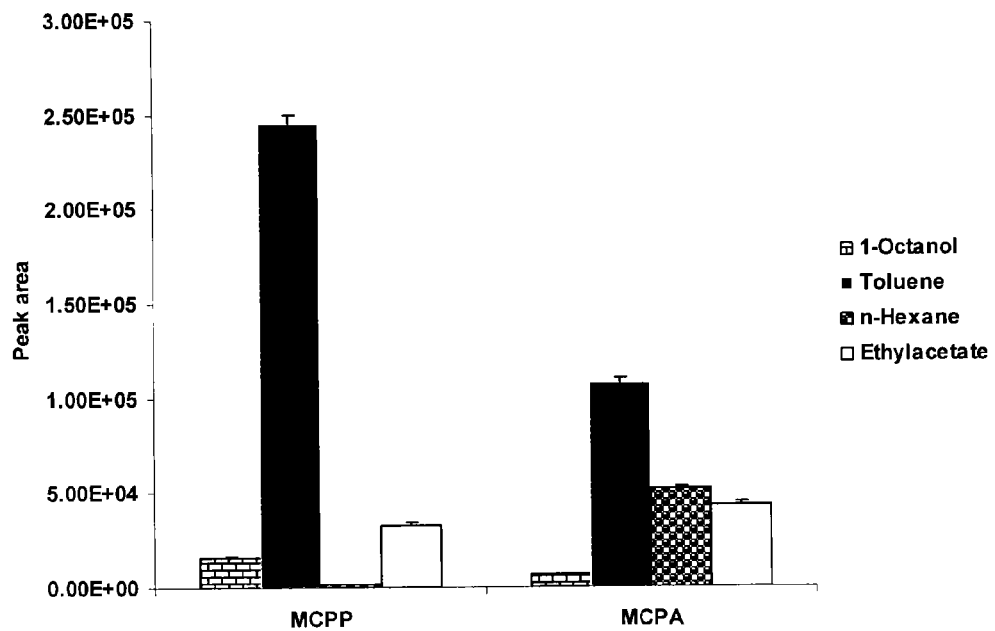
FIG. 2 is a graph of peak area versus extraction solvent for CPE procedure on MCPP and MCPA.

FIG. 2 shows an effect of extraction solvent on the CPE procedure at pH 10, 20 µg l$^{-1}$ analyte concentration, 3.2 ml TBA-OH (0.5 mol l$^{-1}$), 60 min extraction time, 228 mg MeI at 70° C.

From the results obtained in FIG. 2, among the four solvents, toluene was preferable and provided the best outcome. The favored result of toluene may be attributed to the similarity between both analytes and toluene in terms of the presence of an aromatic ring, which improves partitioning into the organic phase. In comparison to toluene, the other three solvents have aliphatic chains in which the charged and polar analytes are less soluble.

Figure 3:
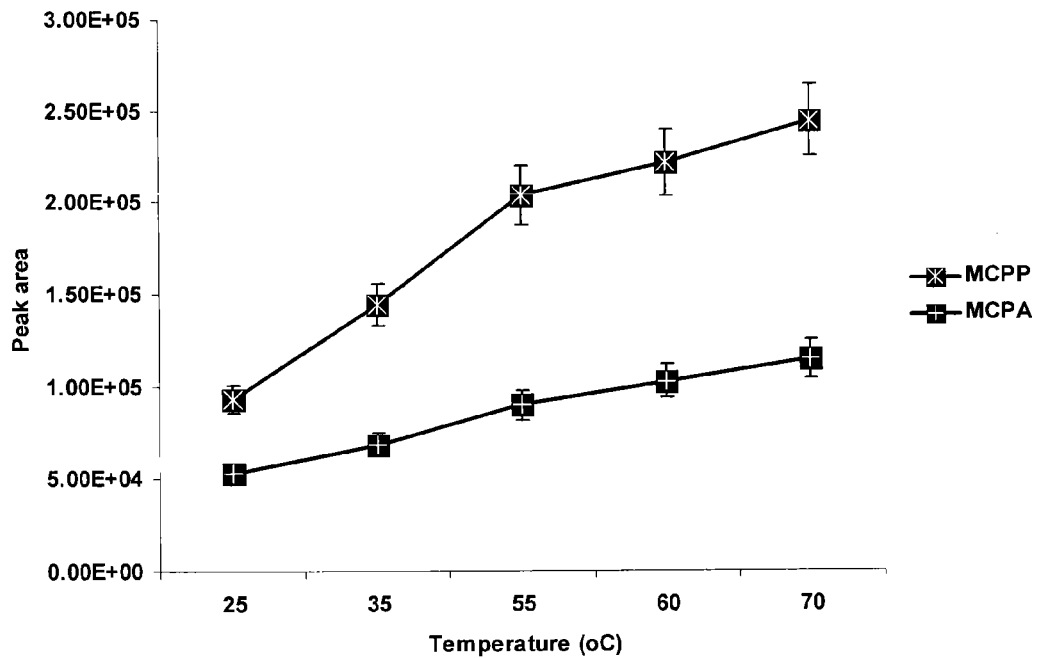
FIG. 3 is a graph of peak area versus temperature for CPE procedure on MCPP and MCPA.

Furthermore, the effect of temperature from 25° C. to 70° C. was investigated. FIG. 3 shows an effect of temperature on the performance of the CPE method at pH 10, 20 µg l$^{-1}$ analyte concentration, 3.2 ml TBA-OH (0.5 mol l$^{-1}$), 60 min extraction time, 228 mg MeI and 500 µl of toluene as extractant solvent.

As shown in FIG. 3, the efficiency of PME and derivatization of analytes increases with an increase in temperature. While the boiling point of ≤290° C. for MCPA is relatively high, that of MCPP is estimated at ≤100° C. However, MCPP decomposes before this point is reached. Therefore, a temperature of 70° C. was adopted for the remaining PME experiments.

Figure 4:
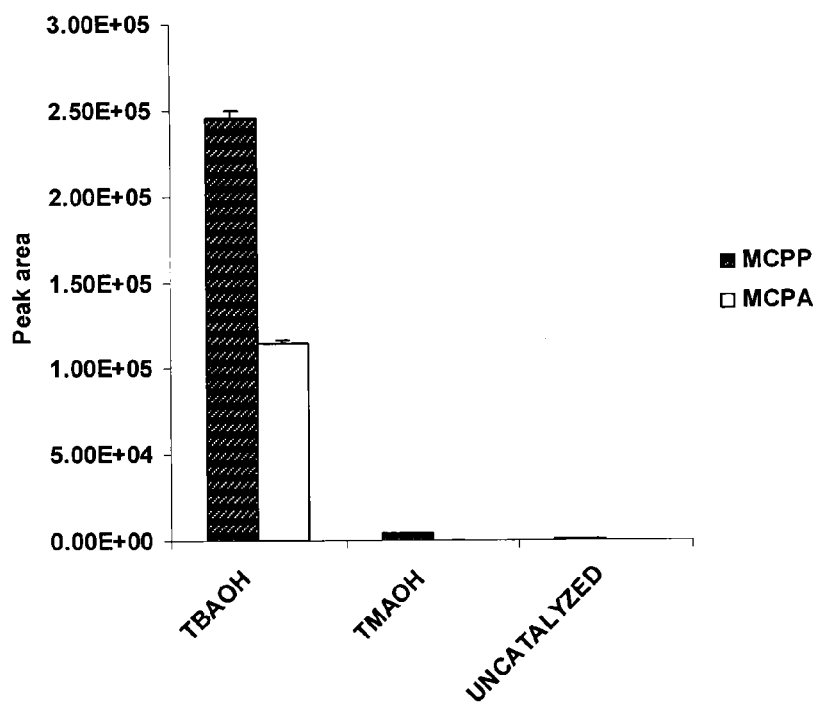
FIG. 4 is a graph of peak area versus PTC reagents or no PTC reagent for CPE procedure on MCPP and MCPA.

The method was further performed with PTC reagents. FIG. 4 shows a comparison between CPE performed without PTC and with two types of PTC reagents at pH 10, 20 µg l$^{-1}$ analyte concentration, 60 min extraction time, 228 mg MeI and 500 µl of toluene as extractant solvent at 70° C.

In FIG. 4, when the PME was performed without the addition of PTC, only MCPP was resolved and its EF was less than when the process was catalyzed, 5.5 and 288 for TMA-OH and TBA-OH, respectively. This is an indication that the type of PTC is also vital to the PME procedure. In this case, TBA-OH was more preferable than TMA-OH by a factor of 52. The better functionality of TBA-OH may be attributed to the bulkier R-group, allowing a better facilitation of the formation of reverse micelle during the phase transfer process (Feitosa, E., Catelam, K. T., Hasmann, F. A., Johansson, H.-O., Roberto, I. C., Pessoa Jr. A., J. Chromatogr B, 2008, 862, 58-63—incorporated by reference in its entirety).

Figure 5:
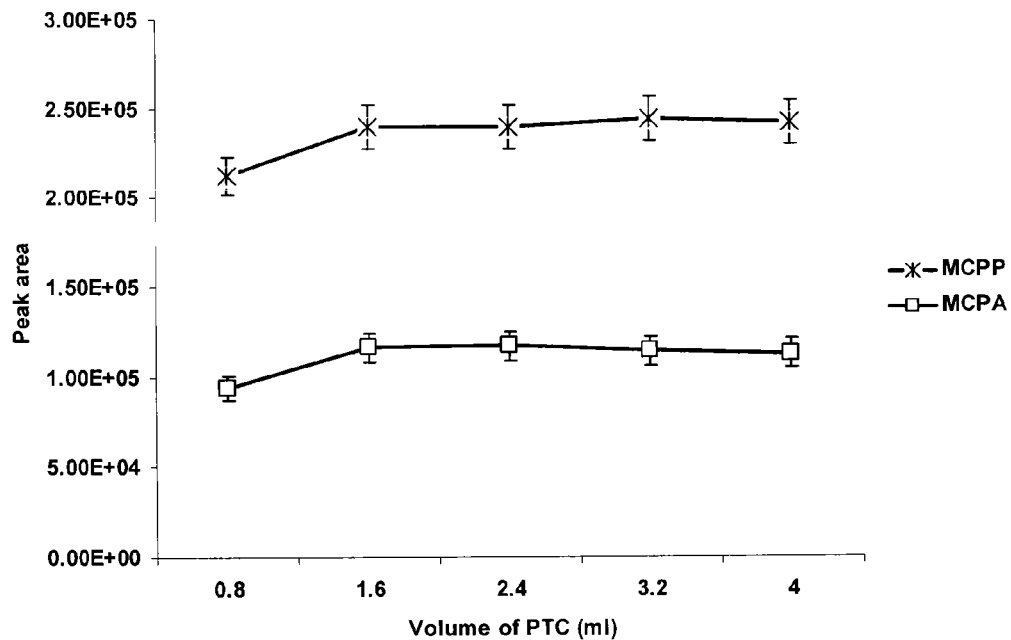
FIG. 5 is a graph of peak area versus volume of PTC in milliliters for CPE procedure on MCPP and MCPA.

On the other hand, PME was also influenced by the volume of the 0.5 $mol\, l^{-1}$ PTC present. Therefore, different volumes between 0.8 ml and 4.0 ml were investigated. FIG. 5 shows an effect of amount of PTC on CPE method at pH 10, 20 $\mu g\, l^{-1}$ analyte concentration, 60 min extraction time, 228 mg MeI and 500 $\mu l$ of toluene as extractant solvent at 70° C. As shown in FIG. 5, optimal performance was achieved at 1.6 ml. Increasing volume beyond this did not appear to significantly enhance the extraction performance.

To assess the effect of derivatization on the analytical determination of the two analytes, PME was performed in the absence of the derivatization reagent.

Figure 6:
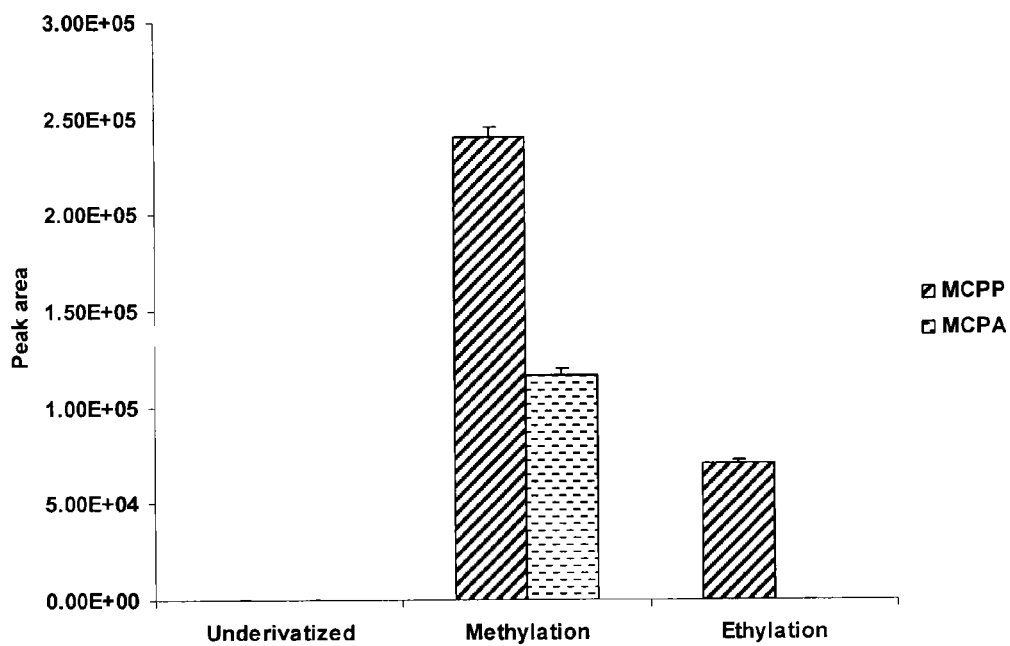
FIG. 6 is a graph of peak area versus derivatization for CPE procedure on MCPP and MCPA.

FIG. 6 shows an effect of derivatization on the CPE method at pH 10, 20 $\mu g\, l^{-1}$ analyte concentration, 1.6 ml TBA-OH (0.5 $mol\, l^{-1}$), 60 min extraction time and 500 $\mu l$ of toluene as extractant solvent at 70° C. As the results shown in FIG. 6 indicate, none of the analytes were resolved. The lack of resolution occurred because these compounds are polar and thus ionize with poor volatility. For such compounds to be compatible with GC determination, they are often derivatized to reduce their polarity and enhance their thermal properties (Framegos, Y. C., Nanos, C. G., Vervoort, J., Stalikas, C. D., J. Chromatogr A, 2004, 1041, 11-18—incorporated by reference in its entirety). Two types of derivatization were tested: methylation with methyl iodide and ethylation with ethyl bromide. As evident from the results, methylation provided the best quantitation for the analytes. Methylation may be ascribed to the effect that iodide is a better leaving group in the typical SN2 reaction and gives a steric advantage for the methyl radical (Bento, A. P., Bickelhaupt, F. M., J. Org. Chem., 2008, 73, 7290-7299—incorporated by reference in its entirety).

Figure 7:
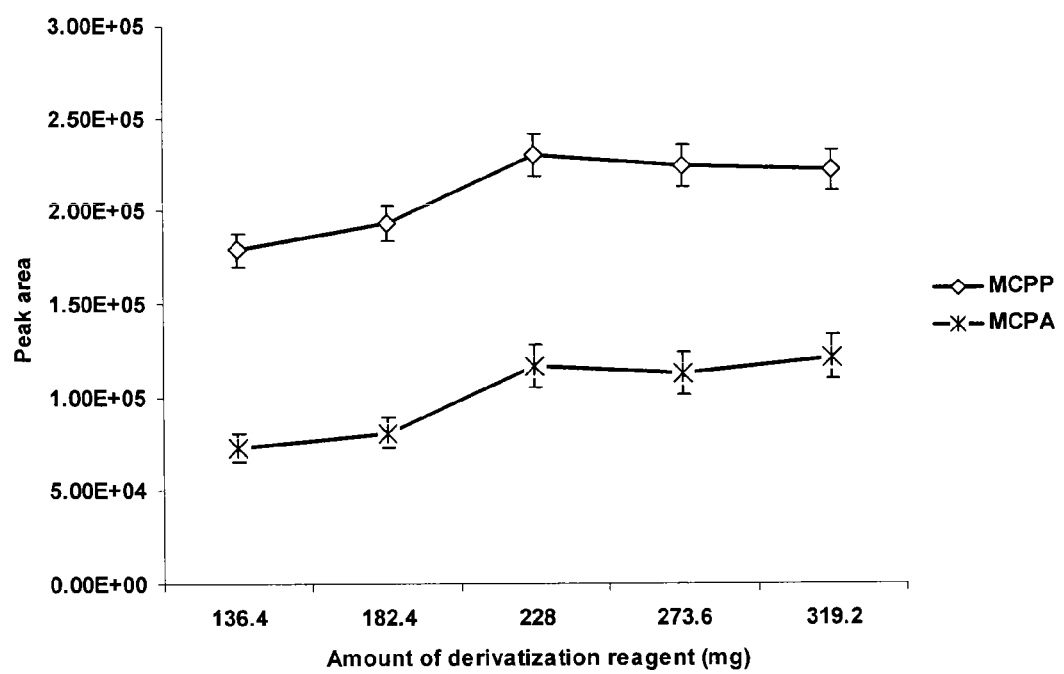
FIG. 7 is a graph of peak area versus amount of derivatization reagent in milligrams for CPE procedure on MCPP and MCPA.

In addition, the effect of the amount of the derivatization reagent was also investigated. FIG. 7 shows an effect of the amount of derivatization reagent on CPE method under experimental conditions of pH 10, 20 $\mu g\, l^{-1}$ analyte concentration, 1.6 ml TBA-OH (0.5 $mol\, l^{-1}$), 60 min extraction time, MeI as derivatization reagent and 500 $\mu l$ of toluene as extractant solvent at 70° C. FIG. 7 shows that optimal performance of the PME derivatization may be achieved with about 228 mg of the derivatization reagent under the experimental conditions. The respective derivatives were confirmed using the NIST 98.L and wiley7n.1 libraries. Molecular ions of MCPA have a m/z equal to 214 and 228 for methylated and ethylated derivatives respectively, while MCPP has 228 and 242 accordingly.

Furthermore, the PME procedure with simultaneous derivatization was performed for different lengths of time from 30 to 90 min. Sharp increase in EF of the analytes was observed as the time was progressively increased from 30 to 60 min, and thereafter, no significant effect could be noticed. Therefore, it appears that 60 min PME time was enough for significant enrichment of the organic phase with the derivatized analytes. This time was then maintained during the course of the remaining experiments.

Method Performance

Performance of the PME derivatization was assessed by utilizing performance indices such as linearity, LOD, and percent relative standard deviation (% RSD). Derivatization and the use of phase transfer catalyst have proven to be especially vital for the resolution of the analytes and their sensitive determination, with an enrichment factor of 288-fold for catalyzed over non-catalyzed procedure. Good linearity was determined between the concentration ranges of 0.1 to 80 $\mu g\, l^{-1}$. MCPA was found to be linear with correlation coefficient of 0.9911, and MCPP displayed linearity between these ranges, with coefficient of 0.9956. Repeatability for these determinations, as represented by % RSD, varied from 0.69 to 12.9 with an average of 7.4 for MCPP and from 4.22 to 8.47 with an average of 5.2 for MCPA (n=3). Low LODs were obtained for the two analytes; 0.80 $ngl^{-1}$ and 3.04 $ngl^{-1}$ for MCPP and MCPA respectively, at signal to noise ratio of three (S/N=3). This indicates the sensitivity of this method to detect very low levels of the analytes in real samples (Pereiro, I. R., Irimia, R. G., Cano, E. R., Torrijos, R. C., Anal Chim Acta, 2004, 524, 249-256; Maloschik, E., Mörtl, M., Székács, A., Anal Bioanal Chem 2010, 397, 537-348—incorporated by reference in its entirety). As presented in Table 1, this method compared favorably with several others in the literature.

TABLE 1

Method performance as compared to literature results

| Method | SV[a] | ET[b] | LOD (ng $l^{-1}$) | % RSD | RR[c] |
|---|---|---|---|---|---|
| LPME-GC-MS | 10 | 40 | 0.51-13.7 | <12.3 | 88.2-105.7 |
| LLLME-LC-UV | 10 | 60 | 0.8-2.2 | 3.2-7.4 | 87-101 |
| SPE-GC-MS | 1000 | >30 | 1-12 | 2-8 | 80-120 |
| SPE-GC-MS | 1000 | ≤100 | 2000-112000 | 3-14.5 | 9-102 |
| *CPE-GC-MS | 10 | 60 | 0.80-3.04 | 0.69-12.9 | 93.2-114.7 |

[a]Sample volume (ml)
[b]Extraction time (min)
[c]recovery/relative recovery (%)
*instant method Real Sample Analysis The applicability of the developed method to the natural setting was examined by carrying out the PME derivatization on four samples. The relative recovery (% RR) calculations, after spiking tap water and seawater with 5 $\mu g l^{-1}$ of the analytes respectively and taking the ratios of the resultant peak areas with ultrapure water, yielded 95.5-105.5% for MCPP and 93.5-104.5% for MCPA in seawater and 91-103% for MCPP and 90.5-105% for MCPA in tap water, respectively, indicating the absence of matrix effect.

TABLE 2

Recovery calculations and real sample analysis results

| Analyte | Matrix | Amount added ($\mu g\, l^{-1}$) | Amount found ($\mu g\, l^{-1}$) | % RSD | % RR |
|---|---|---|---|---|---|
| MCPP | Tap water | 5 | 5.1 | 3.0 | 103 |
| | | 5 | 4.6 | 8.0 | 92 |
| | | 5 | 4.5 | 6.0 | 91 |
| | Seawater | 5 | 4.8 | 4.0 | 96 |
| | | 5 | 5.2 | 5.5 | 105.5 |
| | | 5 | 4.7 | 4.5 | 95.5 |
| | DS-1 | — | 0.84 ± 0.06[a] | — | — |
| | DS-2 | — | 0.27 ± 0.01 | — | — |
| | JS-3 | — | nd[b] | — | — |
| | JS-4 | — | nd | — | — |
| MCPA | Tap water | 5 | 4.5 | 9.5 | 90.5 |
| | | 5 | 5.2 | 5.0 | 105 |
| | | 5 | 4.6 | 8.0 | 92 |

TABLE 2-continued

Recovery calculations and real sample analysis results

| Analyte | Matrix | Amount added (µg l⁻¹) | Amount found (µg l⁻¹) | % RSD | % RR |
|---|---|---|---|---|---|
| | Seawater | 5 | 4.7 | 6.5 | 93.5 |
| | | 5 | 4.9 | 1.5 | 98.5 |
| | | 5 | 5.2 | 4.5 | 104.5 |
| | DS-1 | — | nd | — | — |
| | DS-2 | — | nd | — | — |

$^a$mean ± s.d
$^b$not detected

As can be seen in Table 2, MCPP was found in two of the locations of seawater samples although MCPA was not detected. These two locations were highly polluted and turbid as a result of the inputs from sewage discharge and agricultural run-off water and therefore more likely to indicate levels of MCPP. The concentration (µg l⁻¹) of MCPP found at DS-1 was 0.84±0.06 (mean±s.d.) and 0.27±0.01 at DS-2.

A method for the simultaneous determination of the acidic herbicides MCPP and MCPA was developed based on phase-transfer catalyst assisted phase transfer microextraction. Using this method, high enrichment of the analytes was obtained within a reasonable period of time (60 min). This method displayed good linearity between a wide range of concentrations and is characterized by low LODs which would allow sensitive determinations of these analytes at their low concentrations in the environmental water samples.

The invention claimed is:

1. A method for determining the concentration of a phenoxy herbicide in an aqueous sample, comprising:
    simultaneously phase-transfer catalyst extracting and alkylating an aqueous sample comprising a phenoxy herbicide to form a sample composition, and
    measuring an amount of the alkylated phenoxy herbicide in the sample composition,
    wherein a pH of the aqueous sample throughout the extracting and alkylating is from 7 to 13.

2. The method of claim 1, wherein the phenoxy herbicide is 4-chloro-2-methylphenoxy acetic acid or 4-chloro-2-methylphenoxy propionic acid.

3. The method of claim 1, comprising alkylating the aqueous sample with phase transfer catalysis with a quaternary ammonium compound.

4. The method of claim 1, wherein the pH is 10.

5. The method of claim 1, wherein the phase transfer catalyst extracting comprises extracting the aqueous sample with an extraction solvent selected from the group consisting of 1-octanol, toluene, n-hexane and ethylacetate.

6. The method of claim 5, wherein the extraction solvent is toluene.

7. The method of claim 1, wherein the phase-transfer catalyst extracting is conducted at a temperature of from 25 to 70° C.

8. The method of claim 7, wherein the temperature is about 70° C.

9. The method of claim 1, wherein the phase-transfer catalyst extracting is cloud-point extraction comprising:
    adding a phase transfer catalyst reagent selected from the group consisting of tetramethyl ammonium hydroxide and tetrabutyl ammonium hydroxide to the aqueous sample.

10. The method of claim 9, wherein the phase transfer catalyst reagent is tetrabutyl ammonium hydroxide.

11. The method of claim 9, wherein a volume of the phase transfer catalyst reagent is from 1.4 to 2.4 ml.

12. The method of claim 1, wherein the alkylating comprises methylating with methyl iodide or ethylating with ethyl bromide.

13. The method of claim 12, wherein the alkylating comprises methylating with methyl iodide.

14. The method of claim 1, wherein the measuring is conducted by at least one selected from the group consisting of GC-MS, HPLC/diode array detector, and capillary electrophoresis with ultraviolet detection.

15. The method of claim 14, wherein the measuring is conducted by GC-MS.

* * * * *